(12) United States Patent
Tachikawa et al.

(10) Patent No.: US 10,034,981 B2
(45) Date of Patent: Jul. 31, 2018

(54) SYRINGE AND SYRINGE ASSEMBLY

(75) Inventors: Kouichi Tachikawa, Shizuoka (JP);
Yoichiro Iwase, Kanagawa (JP);
Hirotaka Ohashi, Tokyo (JP); Junichi Ogawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 850 days.

(21) Appl. No.: 14/001,905

(22) PCT Filed: Feb. 13, 2012

(86) PCT No.: PCT/JP2012/053262
§ 371 (c)(1),
(2), (4) Date: Aug. 28, 2013

(87) PCT Pub. No.: WO2012/117837
PCT Pub. Date: Sep. 7, 2012

(65) Prior Publication Data
US 2013/0331798 A1     Dec. 12, 2013

(30) Foreign Application Priority Data

Mar. 1, 2011 (JP) .................................. 2011-044149
Apr. 25, 2011 (JP) .................................. 2011-097340

(51) Int. Cl.
*A61M 5/315* (2006.01)
*A61M 5/28* (2006.01)
*A61M 5/24* (2006.01)

(52) U.S. Cl.
CPC .............. *A61M 5/315* (2013.01); *A61M 5/24* (2013.01); *A61M 5/28* (2013.01)

(58) Field of Classification Search
CPC .. A61M 5/178; A61M 5/315; A61M 5/31566; A61M 5/31578; A61M 5/3158
See application file for complete search history.

(56) References Cited

U.S. PATENT DOCUMENTS 2,860,635 A * 11/1958 Wilburn .................. A61M 5/28
206/365
4,639,248 A    1/1987 Schweblin
(Continued)

FOREIGN PATENT DOCUMENTS

EP       0186232        7/1986
JP    2003-509082       3/2003
(Continued)

OTHER PUBLICATIONS

Office Action issued in Japan Counterpart Patent Appl. No. 2013-502229, dated Aug. 25, 2015, along with an English translation thereof.
(Continued)

*Primary Examiner* — Nathan R Price
*Assistant Examiner* — Weng Lee
(74) *Attorney, Agent, or Firm* — Greenblum & Bernstein, P.L.C.

(57) ABSTRACT

This syringe has an outer tube, a gasket, and a pusher. The pusher is provided with: a tubular holding part which covers at least a part of an outer surface of the outer tube and is movable relative to the outer tube in the longitudinal direction thereof; and a pressure part which is connected with the holding part, is inserted into the outer tube, and moves the gasket to the distal side of the outer tube by distally a movement of the holding part relative to the outer tube. In addition, between the holding part and the outer tube, a guide part is provided which guides the movement of the holding part relative to the outer tube.

11 Claims, 11 Drawing Sheets

(56) References Cited

U.S. PATENT DOCUMENTS

| | | | | |
|---|---|---|---|---|
| 5,176,643 | A | * | 1/1993 | Kramer ............... A61M 5/2033 |
| | | | | 604/135 |
| 7,267,668 | B2 | | 9/2007 | Ruben |
| 2001/0056263 | A1 | * | 12/2001 | Alchas ................... A61M 5/46 |
| | | | | 604/193 |
| 2005/0240159 | A1 | | 10/2005 | Kito et al. |
| 2007/0100290 | A1 | | 5/2007 | Schiffmann et al. |
| 2012/0157965 | A1 | * | 6/2012 | Wotton ............... A61K 31/519 |
| | | | | 604/506 |

FOREIGN PATENT DOCUMENTS

| | | |
|---|---|---|
| JP | 2004-97640 | 4/2004 |
| JP | 2004-526520 | 9/2004 |
| JP | 2005-500871 | 1/2005 |
| JP | 2007/75610 | 3/2007 |
| JP | 2010-502340 | 1/2010 |
| WO | 95/1198 | 1/1995 |
| WO | 00/16829 | 3/2000 |
| WO | 02/083205 | 10/2002 |
| WO | 02/083212 | 10/2002 |
| WO | 2008/029280 | 3/2008 |

OTHER PUBLICATIONS

International Search Report dated Apr. 3, 2012 with English language translation.
Search report from E.P.O., dated Aug. 6, 2014.

* cited by examiner

SYRINGE AND SYRINGE ASSEMBLY

TECHNICAL FIELD

The present invention relates to a syringe and a syringe assembly.

BACKGROUND ART

A syringe, generally, is composed of an outer tube, a gasket capable of sliding in the outer tube, and a plunger operated to move the gasket. In addition, the outer tube has a barrel part, and a reduced-diameter part (port) which is provided on a distal side (tip side) of the barrel part and is reduced in diameter relative to the barrel part. Such a syringe is so configured that the gasket is moved distally by pushing a pusher into the outer tube, whereby a liquid medicine stored in the outer tube is guided through an opening of the port to the exterior of the outer tube (refer to, for example, Patent Document 1).

The syringe described in Patent Document 1 is used, for example, as follows. With a puncture needle connected to the port, a outer tube is gripped with four fingers other than a thumb, and the thumb is put on the pusher. In this condition, the puncture needle is made to puncture a skin, and, while maintaining this state, the pusher is pushed in by the thumb to thereby administer the liquid medicine. Also, with the puncture needle connected to the port, the outer tube is pinched with a index finger and a middle finger, and the thumb is put on the pusher. In this condition, the puncture needle is made to puncture a skin, and, while maintaining this state, the pusher is pushed in by the thumb to thereby administer the liquid medicine.

According to such a using method, however, the liquid medicine cannot be administered without carrying out two steps, namely, one step of making the puncture needle to puncture a skin and maintaining this state and the other step of pushing in the pusher relative to the outer tube while maintaining the position of the outer tube relative to the skin. Besides, operating the pusher is attended by weakening of force for fixing the outer tube, whereby the puncture depth of the needle may be varied. Thus, there are problems that the conventional syringe is poor in operability and is difficult to use.

Patent Document 1: Japanese Patent Laid-open No. 2004-97640

DISCLOSURE OF INVENTION

It is an object of the present invention to provide a syringe and a syringe assembly which are excellent in operability.

In order to attain the above object, the present invention provides a syringe including: an outer tube having a port through which a liquid can flow in and out, and the port provided on a distal side of the outer tube; a gasket capable of sliding in the outer tube; and a pusher operated to move the gasket toward the distal side of the outer tube, wherein the pusher has a tubular holding part configured to cover at least a part of an outer surface of the outer tube and be movable relative to the outer tube in a longitudinal direction of the outer tube, and a pressure part connected with the holding part, inserted into the outer tube, and configured to move the gasket to the distal side of the outer tube by distally a movement of the holding part relative to the outer tube.

In the syringe of the present invention, preferably, a guide part configured to guide the movement of the holding part relative to the outer tube in the longitudinal direction of the outer tube is provided between the holding part and the outer tube.

In the syringe of the present invention, preferably, the guide part is fixed to one of the outer tube and the holding part, and is in slidable contact with the other.

In the syringe of the present invention, preferably, the pressure part is spaced from the gasket in the longitudinal direction of the outer tube.

The syringe of the present invention, preferably, includes spaced state-maintaining means for maintaining a spaced state of the pressure part and the gasket.

The syringe of the present invention, preferably, includes biasing means for biasing the outer tube to the distal end of the outer tube distally relative to the holding part.

In the syringe of the present invention, preferably, the biasing means includes a spring member provided inside the holding part.

In the syringe of the present invention, preferably, the pressure part is spaced from the gasket in the longitudinal direction of the outer tube through biasing by the biasing means.

In the syringe of the present invention, preferably, when an external force of more than a predetermined value for moving the outer tube proximally relative to the holding part is exerted on at least one of the outer tube and the holding part, the spaced state of the pressure part and the gasket is released, and the gasket is moved toward the distal side of the outer tube by the pressure part.

In the syringe of the present invention, preferably, the predetermined value is set to be greater than an external force exerted on the outer tube when a puncture needle connected to the port is made to puncture a skin, with the holding part being held.

The syringe of the present invention, preferably, includes state-maintaining means for maintaining a state in which the holding part has been moved distally relative to the outer tube.

The syringe of the present invention, preferably, includes detachment-preventing means for preventing the outer tube from being detached from the holding part.

In the syringe of the present invention, preferably, the port of the outer tube is protruding from a distal-side opening of the holding part.

In order to attain the above object, the present invention provides a syringe assembly including: the syringe of the present invention; and a puncture needle attached to the port of the flange.

In the syringe assembly of the present invention, preferably, the syringe assembly includes a housing for storing the puncture needle therein, and the housing has a flange making contact with a distal end face of the holding part when the puncture needle is attached to the port of the outer tube in a state of storing the puncture needle in the housing.

BEST MODE FOR CARRYING OUT THE INVENTION

Now, the syringe and the syringe assembly according to the present invention will be described in detail below, based on preferred embodiments shown in the attached drawings.
<First Embodiment>

Figure 1:
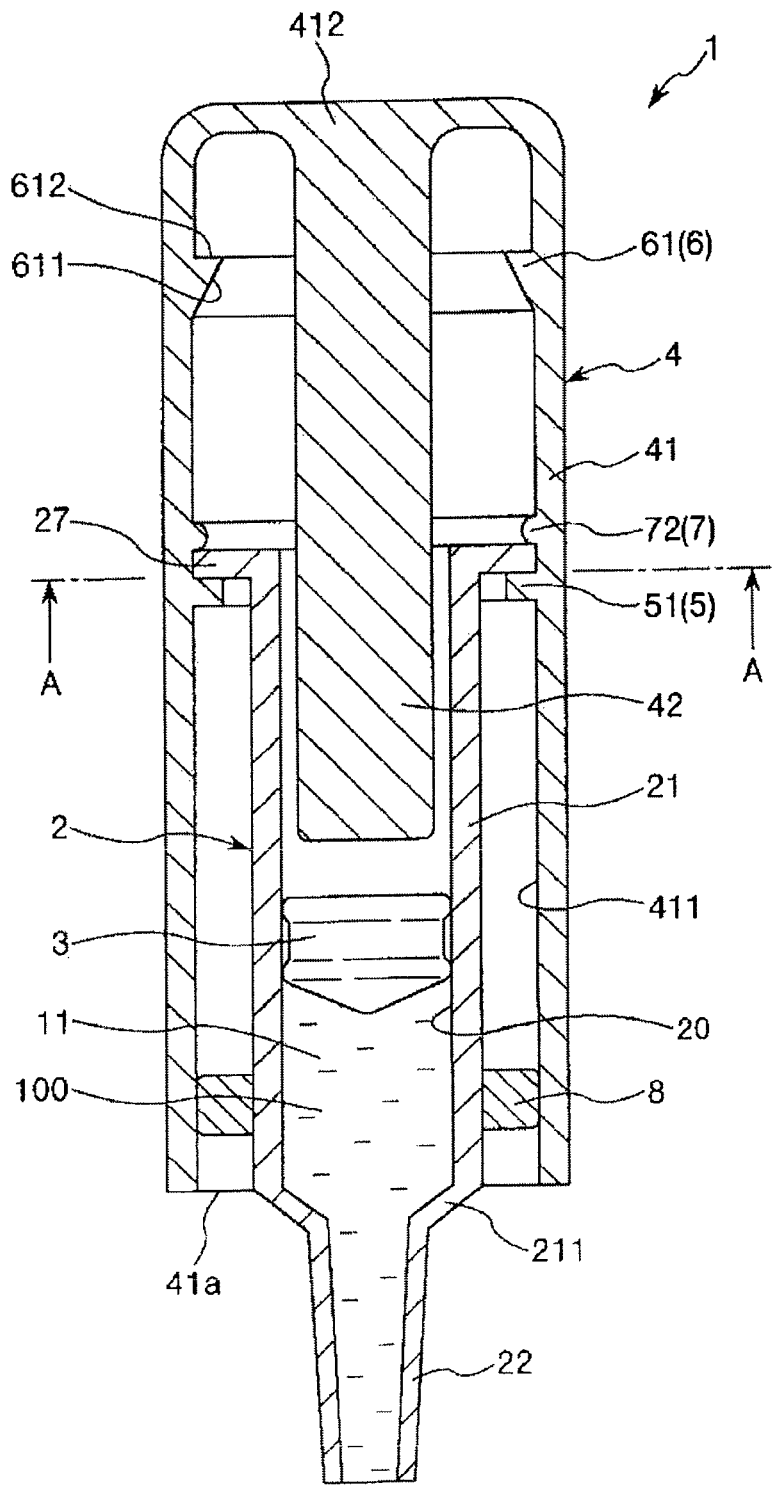
FIG. 1 is a longitudinal sectional view showing a first embodiment of a syringe according to the present invention.
Figure 2:
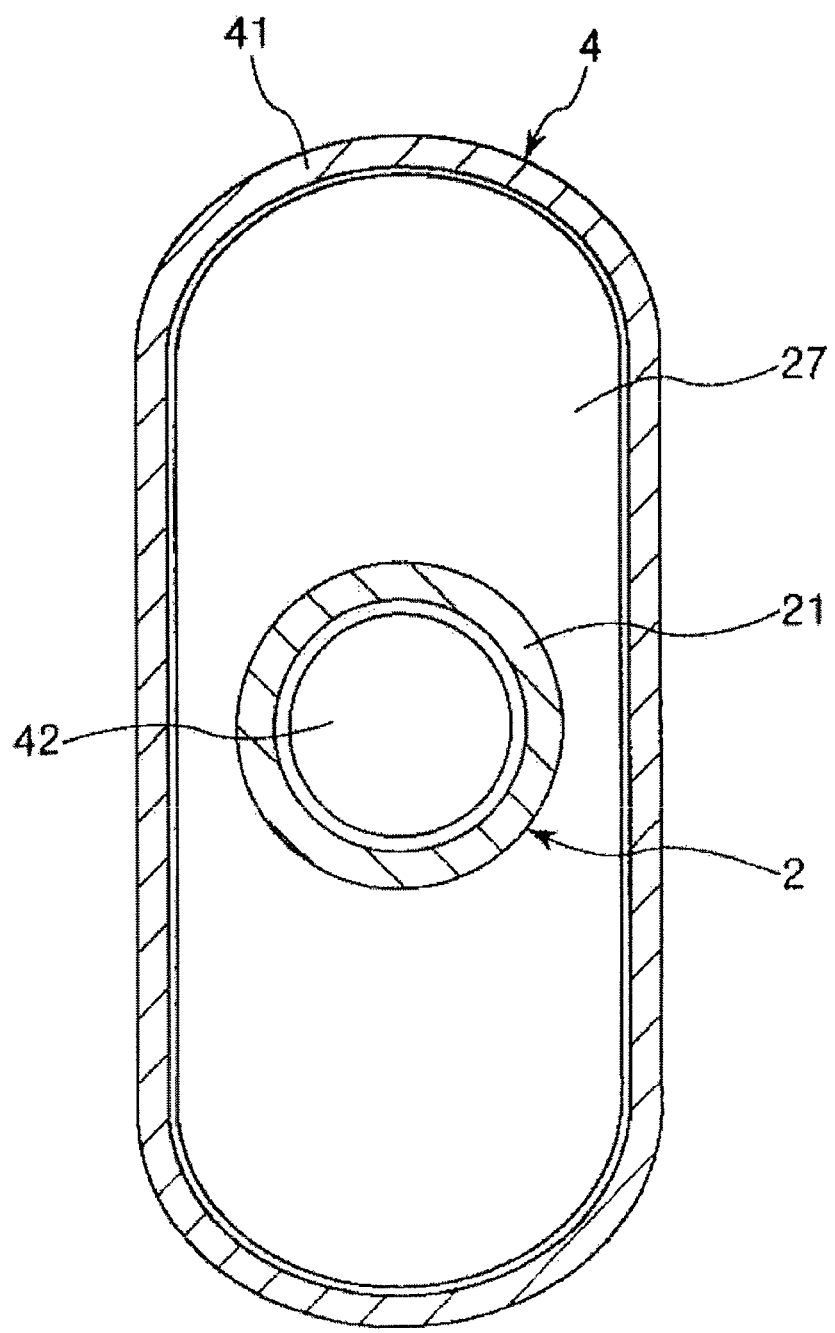
FIG. 2 is a sectional view taken along line A-A in FIG. 1.
Figure 3:
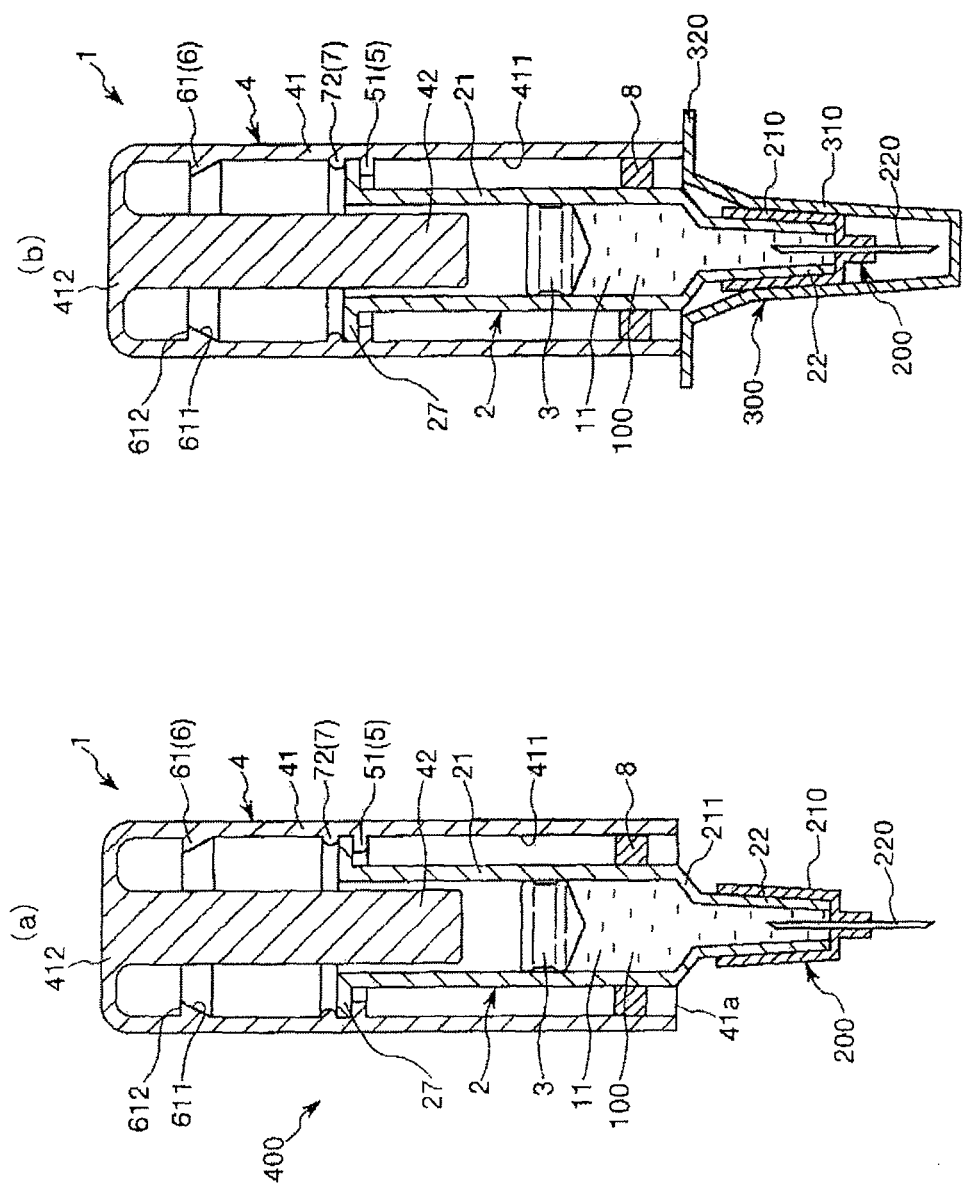
FIG. 3 shows schematic views for illustrating an example of a method of using a syringe assembly according to the present invention in which the syringe shown in FIG. 1 is used.
Figure 4:
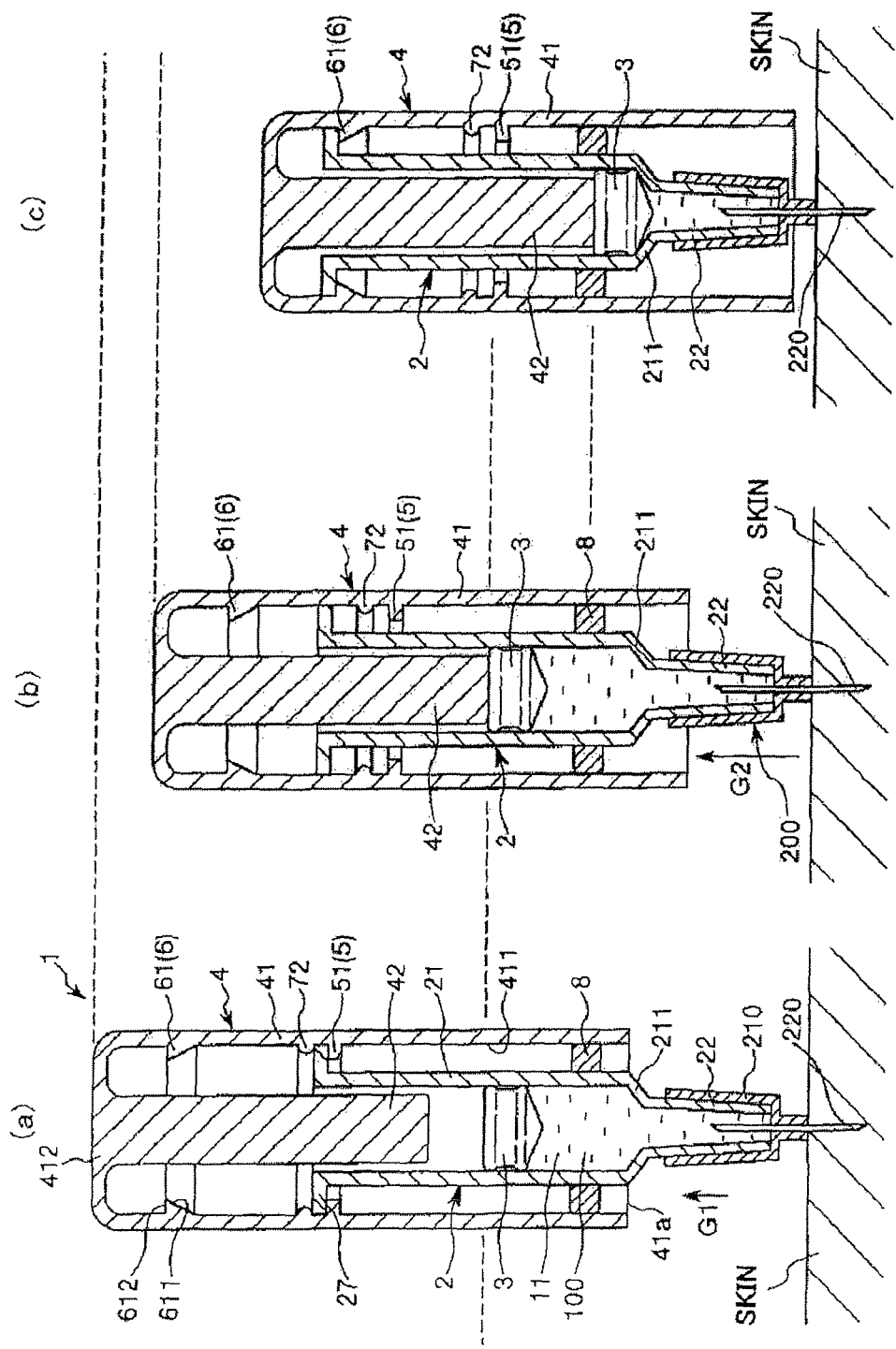
FIG. 4 shows schematic views for illustrating an example of a method of using a syringe assembly according to the present invention in which the syringe shown in FIG. 1 is used.

FIG. 1 is a longitudinal sectional view showing a first embodiment of a syringe according to the present invention, FIG. 2 is a sectional view taken along line A-A in FIG. 1, and FIGS. 3 and 4 show schematic views for illustrating an example of a method of using a syringe assembly according to the present invention in which the syringe shown in FIG. 1 is used. Incidentally, for convenience of description, the upper side in each of FIGS. 1 and 3 will be referred to as "proximal (end)", and the lower side as "distal (end)".

The syringe 1 shown in FIG. 1 is a prefilled syringe in which a liquid medicine 100 is preliminarily stored. Such a syringe 1 is provided with an outer tube 2, a gasket 3 capable of sliding in the outer tube 2, a pusher 4 operated to move the gasket 3, a guide part 8, detachment-preventing means 5, state-maintaining means 6, and spaced state-maintaining means 7.

In this syringe 1, the liquid medicine 100 is preliminarily stored in a space 11 which is surrounded by the outer tube 2 and the gasket 3 and is located on a distal side of the gasket 3. The liquid medicine 100 is not specifically restricted. Examples of the liquid medicine 100 include protein drugs such as antibodies, etc., low molecular proteins, peptide drugs such as hormones, etc., nucleic acid drugs, cell drugs, blood derivatives, vaccines for preventing various infectious diseases, carcinostatic agents, anesthetics, narcotics, antibacterial drugs, steroids, proteinase inhibitors, heparin, saccharide injections such as glucose, etc., electrolyte correction injections such as sodium chloride, potassium lactate, etc., vitamin preparations, lipid emulsions, and contrast mediums (radiopaque materials).

Now, parts of the syringe 1 will be sequentially described in detail below.
—Outer Tube—

The outer tube 2 is composed of a bottomed tubular member. As shown in FIG. 1, the outer tube 2 includes a barrel part 21 having a bottom part 211, a plate-shaped flange 27 provided at an outer surface of a proximal end of the barrel part 21, and a reduced-diameter part 22 which is provided at a central portion of the bottom part 211 and is reduced in diameter relative to the barrel part 21. These parts are formed integrally. In addition, the reduced-diameter part 22 constitutes a port through which a liquid can flow in and out. To the port (reduced-diameter part 22), a needle body hub, a connector or the like is fitted or mounted, as will be described later.

To an opening of the reduced-diameter part 22, for example, a film (not shown) is adhered, or a cap (not shown) is attached, as a sealing member, whereby a lumen of the reduced-diameter part 22 is sealed in an air-tight manner.

Incidentally, the volume of the liquid medicine 100 stored in the outer tube 2 is preferably 0.02 to 2 mL, and more preferably 0.05 to 1.2 mL.

Examples of a material forming the outer tube 2 include resins such as polyvinyl chloride, polyethylene, polypropylene, cyclic polyolefins such as cyclic olefin monopolymers (COP), cyclic olefin copolymers (COC), etc., polystyrene, poly-(4-methylpentene-1), polycarbonate, acrylic resins, acrylonitrile-butadiene-styrene copolymer, polyesters such as polyethylene terephthalate, polyethylene naphthalate, etc., butadiene-styrene copolymer, and polyamides (for example, nylon 6, nylon 6.6, nylon 6.10, nylon 12). Among these resins, preferred from the viewpoint of transparency and easy molding are such resins as polypropylene, cyclic polyolefins, polyesters, and poly-(4-methylpentene-1).

Incidentally, it is preferable for the outer tube 2 to be substantially transparent, for securing inside visibility.
—Gasket—

In the outer tube 2, the gasket 3 formed of an elastic material is stored. At an outer circumferential portion of the gasket 3, a plurality of ring-shaped projections are formed over the whole circumference. With these projections slid in close contact with an inner circumferential surface 20 of the outer tube 2, liquid-tightness is maintained more assuredly, and enhanced sliding properties can be contrived.

The material forming the gasket 3 is not specifically restricted. Examples of the material include elastic materials such as various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, and mixtures of them.
—Pusher—

The pusher 4 is provided to be movable relative to the outer tube 2 in a longitudinal direction of the outer tube 2. As shown in FIG. 1, the pusher 4 is composed of a holding part 41 to be held by a user, and a pressure part 42 which presses the gasket 3. Incidentally, in the following, the state shown in FIG. 1 will be referred to also as an "unused state," for convenience of description.

The pressure part 42 is rod-like in shape, and is inserted in the outer tube 2, its distal-side portion first. In addition, the pressure part 42 is connected with a bottom part 412 of the holding part 41 at a proximal portion thereof. The pressure part 42 as just-mentioned is formed integrally with the holding part 41.

As shown in FIG. 1, the pressure part 42 is spaced from the gasket 3 in the longitudinal direction of the outer tube 2, in the unused state. Therefore, when the pusher 4 is moved by a predetermined distance toward the distal side relative to the outer tube 2, starting from the unused state, the pressure part 42 comes into contact with the gasket 3. When the pusher 4 is further moved distally relative to the outer tube 2 starting from this condition, the pressure part 42 presses the gasket, whereby the gasket 3 is moved toward the distal side of the outer tube 2. With the configuration in which the pressure part 42 is thus spaced from the gasket 3 in the unused state, reliability and safety of the syringe 1 are enhanced, as will be described later.

The holding part 41 is in the shape of a bottomed tube having the bottom part 412, and is covering the whole region of a circumference of the outer tube 2. With the holding part 41 formed in such a shape, the syringe 1 becomes easy to hold, and operability of the syringe 1 is enhanced.

In addition, the holding part 41 is so configured that the reduced-diameter part 22 of the outer tube 2 protrudes from its opening 41*a*, in the unused state. With the reduced-diameter part 22 protruded from the holding part 41 in the unused state, it becomes easy to attach a needle body hub, a connector or the like to the reduced-diameter part 22, as will be described later.

An inner wall 411 of the holding part 41 is in contact with an outer circumferential surface of the flange 27 of the outer tube 2. When the holding part 41 and the outer tube 2 are put into relative movement in the longitudinal direction of the outer tube 2, the outer circumferential surface of the flange 27 and the inner wall 411 of the holding part 41 slide on each other. Therefore, at a proximal portion of the holding part 41, chattering relative to the outer tube 2 can be restrained, and relative movement of the holding part 41 and the outer tube 2 can be performed smoothly.

Besides, the holding part 41 is so configured that the outer tube 2 cannot be rotated therein in a circumferential direction. This ensures that unintentional displacement of the outer tube 2 relative to the holding part 41 can be restrained, and the operability of the syringe 1 is enhanced accordingly. In this embodiment, as shown in FIG. 2, an internal shape of the holding part 41 is set to be a roughly corner-rounded rectangular shape (oval shape), and a shape of the flange 27 is set to correspond to this internal shape, whereby rotation of the outer tube 2 inside the holding part 41 is prevented. Incidentally, the configuration for preventing rotation of the outer tube 2 is not restricted to this. For instance, a configuration may be adopted wherein a projection projecting from the inner wall 411 is formed, and the projection and the outer tube 2 are put in contact with each other, whereby rotation of the outer tube 2 is restrained.

In addition, the holding part 41 is so configured as to restrain the syringe 1 from rolling in the circumferential direction. The safety of the syringe 1 is enhanced accordingly. In this embodiment, as shown in FIG. 2, a external shape of the holding part 41 is set to be a roughly corner-rounded rectangular shape (oval shape) substantially similar to an internal shape, and a part of the outer surface is composed of a plane, whereby the syringe 1 is restrained from rolling. Especially, the holding part 41 shaped as shown in FIG. 2 has such a shape that it can be easily held by the user; therefore, the syringe 1 can be restrained from rolling, and operability of the syringe 1 is enhanced. Incidentally, the configuration for restraining the syringe 1 from rolling is not restricted to this; for example, a configuration may be adopted in which a projection is formed on the outer surface of the holding part 41.

Incidentally, the overall length of the holding part 41 is not specifically limited so long as the holding part 41 can be held. The overall length is preferably 30 to 200 mm, and more preferably 60 to 120 mm. In addition, the diametrical size of the holding part 41 is not particularly limited, insofar as the holding part 41 can be held. The diametrical size is preferably 8 to 70 mm, and more preferably 10 to 30 mm.

Besides, the holding part 41 is preferably so configured that the outer tube 2 disposed in the inside thereof can be visually checked. This enables visual checking of the state of the liquid medicine 100 stored in the outer tube 2 and movements of the gasket 3, resulting in that operability and safety of the syringe 1 are enhanced. Such a configuration is not specifically restricted; for example, a method may be adopted in which the holding part 41 is formed from a substantially transparent material. In addition, where the holding part 41 is colored, the holding part 41 may be provided with an elongate window part extending in the longitudinal direction thereof so that the inside can be visually checked through the window part. Incidentally, the window part may be composed of a transparent member, or may be composed of a through-hole.

While the pusher 4 has been described above, a material forming the pusher 4 is not specifically restricted. Examples of the material include various resins such as polyvinyl chloride, polyethylene, polypropylene, polystyrene, poly-(4-methylpentene-1), polycarbonate, acrylic resins, an acrylonitrile-butadiene-styrene copolymer, polyesters such as polyethylene terephthalate, polyethylene naphthalate, etc., a butadiene-styrene copolymer, polyacetal, and polyamides (for example, nylon 6, nylon 6.6, nylon 6.10, nylon 12). Among these materials, preferred from the viewpoint of easy molding are such resins as polypropylene, polyesters, and poly-(4-methylpentene-1).

—Guide Part—

The guide part 8 has the function of guiding relative movements (movements in the longitudinal direction of the outer tube 2) of the outer tube 2 and the holding part 41. With such a guide part 8 provided, it is possible, for example, to smoothly move the holding part 41 relative to the outer tube 2, so that operability of the syringe 1 is enhanced.

The guide part 8 is provided between the outer tube 2 and the holding part 41. In addition, the guide part 8 is fixed to the outer tube 2, and is located on a side of a distal end of the barrel part 21. The guiding part 8 is annular (ring-like) in shape, and the outer tube 2 is inserted and passed inside the guiding part 8. With the outer tube 2 pressed into the inside of the guiding part 8, for example, it is possible to fix the guiding part 8 to the outer tube 2. Incidentally, the guiding part 8 may be fixed to the outer tube 2 with an adhesive or the like.

Besides, in the unused state, the guide part 8 is in contact with a distal portion of the inner wall 411 of the holding part 41. In addition, when the holding part 41 and the outer tube 2 are relatively moved in the longitudinal direction of the outer tube 2, the inner wall 411 and an outer circumferential surface of the guide part 8 slide on each other. Therefore, at a distal portion of the holding part 41, chattering relative to the outer tube 2 is restrained, so that the relative movement of the holding part 41 and the outer tube 2 can be performed smoothly.

Incidentally, the term "chattering" hereinabove means other displacements than the movements of the holding part 41 and the outer tube 2 in the longitudinal direction of the outer tube 2, or displacements in directions orthogonal to the longitudinal direction of the outer tube 2 and directions inclusive of the orthogonal directions.

Especially, in the syringe 1, the chattering of the distal portion of the holding part 41 is restrained by the guide part 8. Therefore, the movement of the holding part 41 with its distal portion on a forward side in the moving direction, namely, the movement of the holding part 41 toward the distal side of the outer tube 2, can be performed more smoothly. Accordingly, operability of the syringe 1 is enhanced.

Furthermore, in the syringe 1, not only the chattering of the distal portion of the holding part 41 is restrained by the guide part 8, but also the chattering of a proximal portion of the holding part 41 is restrained by the flange 27. Thus, both end portions of the holding part 41 are restrained from chattering. Therefore, relative movement of the holding part 41 and the outer tube 2 can be performed more smoothly.

A material forming the guide part 8 configured as above is not specifically restricted. For example, the same materials as those for the outer tube 2 can be used.

Incidentally, the shape of the guide part 8 is not restricted to the annular (ring-like) shape as in this embodiment, insofar as the function of the guide part 8 can be exhibited. For instance, a configuration may be adopted in which a plurality of guide parts 8 are provided and spaced from each other along the circumferential direction of the outer tube 2. Besides, the guide part 8 may be formed as one body with the outer tube 2.

In addition, in this embodiment, the guiding part 8 is fixed to the outer tube 2, and is slidable relative to the inner wall 411 of the holding part 41. However, a reverse configuration may also be adopted in which the guide part 8 is fixed to the holding part 41, and is slidable relative to the outer wall of the outer tube 2. Besides, in this case, the guiding part 8 may be formed as one body with the holding part 41.

—Detachment-Preventing Means—

The detachment-preventing means 5 has the function of preventing detachment of the outer tube 2 from the holding part 41. As shown in FIG. 1, the detachment-preventing means 5 is composed of a projection 51 provided on the holding part 41. The projection 51 is provided on the opening 41a side, relative to the flange 27 of the inner wall 411 of the holding part 41. With the projection 51 making contact with the flange 27, the outer tube 2 cannot move more toward the opening 41a side. This prevents detachment of the outer tube 2 from the holding part 41.

Where the detachment-preventing means 5 as above is provided, it is possible to obviate such accidents as an accident of falling of the outer tube 2 from the holding part 41 and the resultant breakage of the outer tube 2 by the impact of the falling. Accordingly, operability and safety of the syringe 1 are enhanced.

A shape of the projection 51 is not specifically restricted, insofar as the above-mentioned function can be exhibited. For instance, the projection 51 is provided in a ring-like shape over the whole range in the circumferential direction of the inner wall 411. In addition, a configuration may also be adopted in which a plurality of projections 51 are provided and spaced from each other along the circumferential direction of the inner wall 411. Incidentally, the projection 51 may be formed as one body with the holding part 41. Or, alternatively, the projection 51 may be formed as a separate member and be fixed to the holding part 41 by use of an adhesive or the like.

—State-Maintaining Means—

The state-maintaining means 6 has the function of maintaining a state wherein the holding part 41 has been moved distally relative to the outer tube 2, as compared with its position in the unused state. Specifically, the state-maintaining means 6 has the function of restraining the holding part 41 from moving proximally relative to the outer tube 2, after the holding part 41 is moved distally relative to the outer tube 2 by more than a predetermined distance.

As shown in FIG. 1, the state-maintaining means 6 is composed of a projection 61 provided on the holding part 41. The projection 61 is provided to be located, in the unused state, on the proximal side relative to a position of contact with the flange 27 of the inner wall 411. When the flange 27 gets over the projection 61 due to a distal movement of the holding part 41 relative to the outer tube 2, the flange 27 abuts on the projection 61, whereby the holding part 41 is restrained from moving proximally relative to the outer tube 2.

Especially, of the projection 61, a lower surface (first surface) 611 with which the holding part 41 makes contact when moving distally relative to the outer tube 2 is inclined relative to the longitudinal direction of the outer tube 2, and an upper surface (second surface) 612 with which the holding part 41 makes contact when moving proximally relative to the outer tube 2 is orthogonal to the longitudinal direction of the outer tube 2. Therefore, when the holding part 41 moves distally relative to the outer tube 2, the flange 27 can get over the projection 61 easily. On the contrary, when the holding part 41 moves proximally relative to the outer tube 2, the flange 27 cannot get over the projection 61.

Where the state-maintaining means 6 as above is provided, operability of the syringe 1 is enhanced, as will be described later.

—Spaced State-Maintaining Means—

In the syringe 1, in the unused state, the pressure part 42 and the gasket 3 are spaced from each other, as required. The spacing distance is not particularly limited, and is preferably 0 to 20 mm, and more preferably 3 to 7 mm.

The spaced state-maintaining means 7 has the function of maintaining a spaced state of the pressure part 42 and the gasket 3 when it is necessary to maintain the spaced state of them in the unused state.

As shown in FIG. 1, the spaced state-maintaining means 7 is composed of a projection (contact part) 72 provided on the inner wall 411 of the holding part 41. This enables easy configuration of the spaced state-maintaining means 7.

The projection 72 is provided to be located, in the unused state, on the proximal side relative to the position of contact with the flange 27 of the inner wall 411 and on the distal side relative to the projection 61. The contact between such a projection 72 and the flange 27 restrains the outer tube 2 and the holding part 41 from relatively moving more in such direction that the pressure part 42 and the gasket 3 approach each other. This ensures that the spaced state of the pressure part 42 and the gasket 3 is maintained.

Particularly, as shown in FIG. 1, the projection 72 is preferably provided to be located, in the unused state, at a position for making contact with the upper surface (on the side opposite to the projection 51) of the flange 27. In other words, it is preferable to adopt a configuration wherein the flange 27 is clamped between the projection 72 and the projection 51 in the unused state. This ensures that the outer tube 2 and the holding part 41 are fixed, in the unused state. Therefore, it is possible to prevent unintentional relative movements of the holding part 41 and the outer tube 2, for example, a distal or proximal movement of the outer tube 2 relative to the holding part 41 due to its own weight when the holding part 41 is held. Consequently, operability and safety of the syringe 1 are enhanced.

Incidentally, when an external force (for example, an external force G2 to be described later) of more than a predetermined value in a direction for causing the pressure part 42 and the gasket 3 to approach each other is exerted on at least one of the outer tube 2 and the holding part 41, the flange 27 gets over the projection 72, making it possible for the pressure part 42 to press the gasket 3. The spaced state of the pressure part 42 and the gasket 3 is maintained until an external force of more than the predetermined value is exerted in this manner, whereby operability and safety of the syringe 1 are enhanced, as will be described later.

The shape of the projection 72 is not specifically restricted, so long as the above-mentioned function can be exhibited. For instance, the projection 72 is formed in a ring-like shape provided over the whole range in the circumferential direction of the inner wall 411. Besides, a configuration may also be adopted in which a plurality of projections 72 are provided and spaced from each other along the circumferential direction of the inner wall 411. Incidentally, the projection 72 may be formed as one body with the holding part 41, or may be formed as a separate member and be fixed to the holding part 41 by use of an adhesive or the like.

Thus, the configuration of the syringe 1 has been described in detail above.

Now, an example of a method of using the syringe 1 will be described below, based on FIGS. 3 and 4. Incidentally, the method of using the syringe 1 described below is a method in which the syringe 1 is used for "intracutaneous injection" for administering a liquid medicine 100 between a cuticle and a derma, but this is not restrictive of the method of using the syringe 1. For instance, the syringe 1 may be used for hypodermic injection or intramuscular injection.

As shown in FIG. 3(a), first, an intracutaneous needle (puncture needle) 200 is attached to the reduced-diameter part 22 of the outer tube 2. As a result, a syringe assembly (syringe assembly according to the present invention) 400 is obtained. The intracutaneous needle 200 has a needle body 220, and a hub 210 which supports the needle body 220. The intracutaneous needle 200 is attached to the syringe 1 by fixing the hub 210 to the reduced-diameter part 22 by screw engagement, fitting or the like. Of the syringe 1, the reduced-diameter part 22 is protruding from the holding part 41, so that mounting of the intracutaneous needle 200 can be carried out easily.

The length of the needle body 220 (the length of a part protruding from the hub 210) is not particularly limited, and varies depending on the purpose. In the case of use for the intracutaneous injection as in this embodiment, the length is preferably equal to or lower than 25 mm, and more preferably about 0.5 to 20 mm.

In addition, the outside diameter of the needle body 220 is also not particularly limited, and differs depending on the purpose. In the case of use for intracutaneous injection as in this embodiment, the outside diameter is preferably equal to or lower than 22 G, and more preferably 34 to 26 G, on a basis of the ISO medical needle tube standard.

Incidentally, when mounting the intracutaneous needle 200 to the syringe 1, a case (housing) 300 for exclusive use such as the one shown in FIG. 3(b) may be used. The case 300 has a housing part 310 having an opening, and a flange 320 provided around the opening. In the housing 310, the intracutaneous needle 200 is accommodated so that the hub 210 is disposed on a side of the opening. When the hub 210 is connected to the reduced-diameter part 22, with the intracutaneous needle 200 contained in the case 300, the flange 320 makes contact with a distal end face of the holding part 41. Therefore, exertion of an excessive force (a force which presses the outer tube 2 proximally relative to the holding part 41) on the reduced-diameter part 22 can be prevented. If an excessive force is exerted on the reduced-diameter part 22, the flange 27 would get over the projection 72. Furthermore, the gasket 3 may be pressed by the pressure part 42. Consequently, reliability of the syringe 1 is lowered.

Next, as shown in FIG. 4(a), while holding the holding part 41, the needle body 220 is made to puncture a skin in a direction substantially orthogonal to the skin surface. The manner in which the holding part 41 is held is not specifically restricted. For instance, the holding part 41 may be held in the manner of gripping it or in the manner of pinching it.

In this case, due to resistance generated by puncturing of the skin with the needle body 220, an external force G1 is exerted on the outer tube 2. Under the external force G1, however, the flange 27 cannot get over the projection 72, and a state in which the flange 27 is in abutment on the projection 72 is maintained. In other words, if the needle body 220 is only made to puncture the skin, the gasket 3 is not pressed by the pressure part 42 but is maintained at an unused-state position. This ensures that the liquid medicine 100 is prevented from being ejected through the needle body 220 before the needle body 220 is made to puncture the skin completely. Consequently, operability and safety of the syringe 1 are enhanced.

Subsequently, as shown in FIG. 4(b), the holding part 41 is pushed toward the skin side. This ensures that the external force G2 in the same direction as the external force G1 and greater than the external force G1 is exerted on the outer tube 2, causing the flange 27 to get over the projection 72. As a result, the holding part 41 can be moved distally relative to the outer tube 2. Attendant on a distal movement of the holding part 41, the pressure part 42 approaches the gasket 3, and the pressure part 42 comes into contact with the gasket 3. In other words, a spaced state of the pressure part 42 and the gasket 3 is released when the external force G2 is exerted.

Next, as shown in FIG. 4(c), the holding part 41 is pushed further toward the skin side, whereon the gasket 3 is moved distally by the pressure applied by the pressure part 42. As a result, the liquid medicine 100 stored in the outer tube 2 is injected into the skin via a distal end of the needle body 220.

Here, in a used state in which the gasket 3 has completely been moved toward the distal side of the outer tube 2 (in a state in which the gasket 3 and the bottom part 211 make contact with each other and administration of the liquid medicine 100 is finished), the flange 27 has gotten over the projection 61. Therefore, after the used state is established, the holding part 41 cannot be moved proximally relative to the outer tube 2, namely, cannot return into the unused state.

Incidentally, a timing for the flange 27 to get over the projection 61 may be before the gasket 3 is completely moved toward the distal side of the outer tube 2, but, preferably, the timing is substantially simultaneous with the completion of distal movement of the gasket 3. In other words, the state-maintaining means 6 is preferably so configured as to maintain a positional relationship between the outer tube 2 and the holding part 41 at the moment of completion of the movement of the gasket 3 relative to the outer tube 2. This ensures that appropriate completion of the administration of the liquid medicine 100 can be confirmed by the feeling or sound generated at the time when the flange 27 gets over the projection 61. Therefore, appropriate administration of the liquid medicine 100 can be performed. In addition, troubles such as a trouble in which the holding part 41 is pushed toward the skin side by an excessive force notwithstanding the administration is completed can be prevented from occurring. Thus, reliability and safety of the syringe 1 are enhanced.

Finally, for withdrawing the needle body 220 from the skin, the holding part 41 is moved so as to be spaced away from the skin surface. As has been mentioned above, the used state is being maintained by the projection 61. This ensures that at the time of withdrawing the needle body 220 from the skin, the outer tube 2 and the holding part 41 are prevented from being displaced in an unprepared manner, and the needle body 220 can be withdrawn safely. Accordingly, operability and safety of the syringe 1 are enhanced.

According to the syringe 1 as above, puncturing of the skin by the needle body 220 and the administration of the liquid medicine 100 can be carried out by only the operation of holding the holding part 41 and pushing it toward the skin side. In other words, the syringe 1 enables the administration of the liquid medicine 100 to be completed in one step. In addition, according to the syringe 1, the intracutaneous injection of the liquid medicine 100 can be achieved by use of an arm's force, so that the syringe can be operated with a sufficient force. Consequently, the syringe 1 is excellent in operability.

<Second Embodiment>

Now, a second embodiment of the syringe according to the present invention will be described below.

Figure 5:
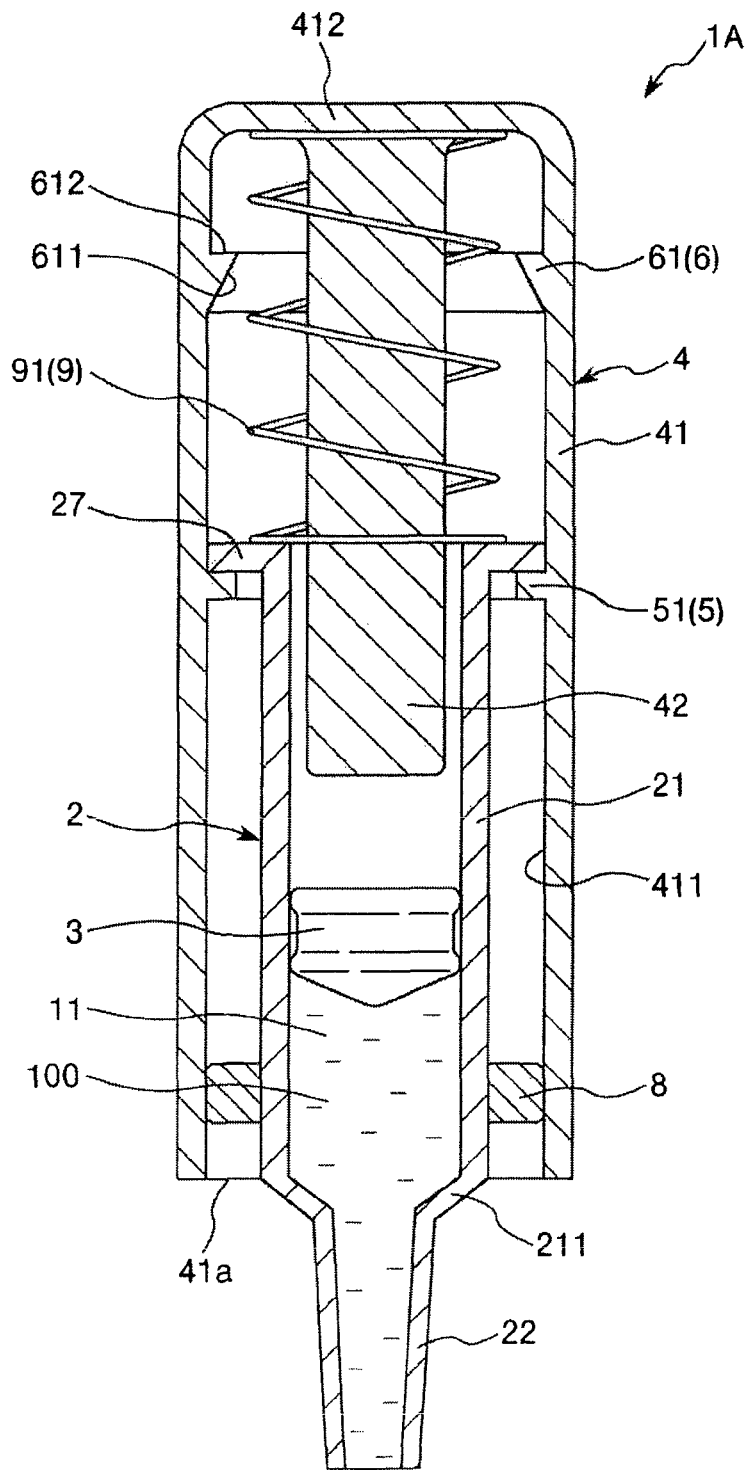
FIG. 5 is a longitudinal sectional view showing a second embodiment of a syringe according to the present invention.
Figure 6:
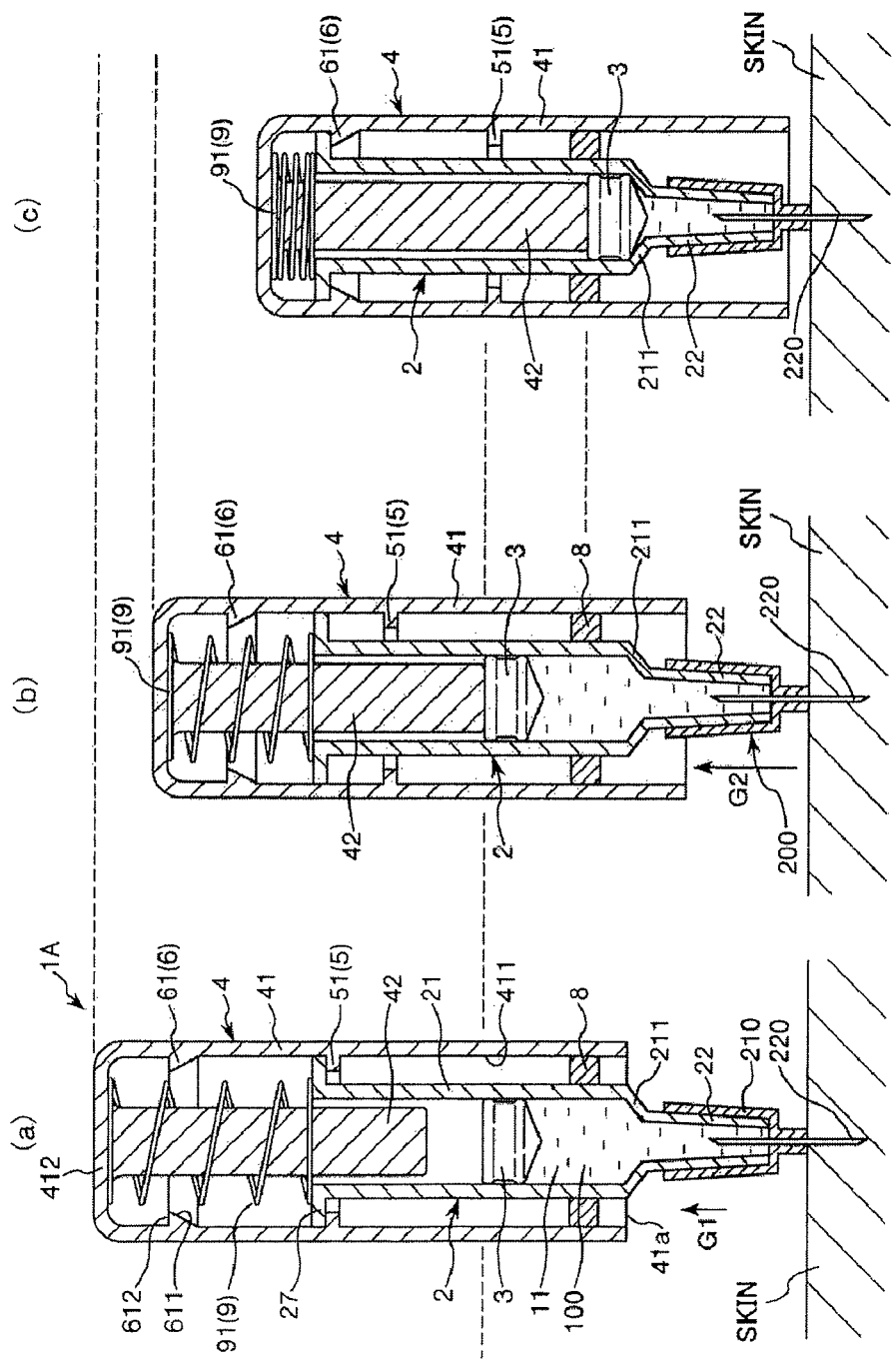
FIG. 6 shows schematic views for illustrating an example of a method of using a syringe assembly according to the present invention in which the syringe shown in FIG. 5 is used.

FIG. 5 is a longitudinal sectional view showing a second embodiment of a syringe according to the present invention, and FIG. 6 shows schematic views for illustrating an example of a method of using a syringe assembly according to the present invention in which the syringe shown in FIG. 5 is used.

Now, the syringe according to this embodiment will be described below. The following description will be made to center on differences from the syringe according to the first embodiment above, and descriptions of the same items as those in the first embodiment will be omitted.

The syringe in this embodiment is substantially the same as the syringe in the first embodiment above, except for spaced state-maintaining means is omitted and biasing means is provided in place thereof.

The syringe 1A shown in FIG. 5 is a prefilled syringe with a liquid medicine 100 preliminarily stored therein. Such a syringe 1A includes an outer tube 2, a gasket 3 capable of sliding in the outer tube 2, a pusher 4 operated to move the gasket 3, a guide part 8, detachment-preventing means 5, state-maintaining means 6, and biasing means 9.

Incidentally, the outer tube 2, the gasket 3, the pusher 4, the guide part 8, the detachment-preventing means 5 and the state-maintaining means 6 are correspondingly the same in configuration as those in the above-described first embodiment, and, therefore, descriptions of them will be omitted.

—Biasing Means—

The biasing means 9 has the function of biasing the outer tube 2 toward a distal side of a holding part 41. With such biasing means 9 provided, it is possible in the unused state to maintain a relative positional relationship of the outer tube 2 and the holding part 41. Specifically, the relative positional relationship of the outer tube 2 and the holding part 41 is maintained without being influenced by the posture (attitude) of the syringe 1A. Accordingly, operability of the syringe 1A is enhanced.

Besides, in the syringe 1A, a pressure part 42 and the gasket 3 are spaced from each other in the unused state, as above-mentioned. The biasing means 9 also has the function of maintaining a state in which the pressure part 42 and the gasket 3 are spaced from each other. As such biasing means 9, various elastic bodies can be used.

As shown in FIG. 5, the biasing means 9 in this embodiment is composed of a spring member 91. This simplifies the configuration of the biasing means 9.

The spring member 91 is provided in the inside of the holding part 41, and between a bottom part 412 of the holding part 41 and a flange 27 of the outer tube 2. The spring member 91 biases the outer tube 2 distally relative to the holding part 41, whereby a state in which the flange 27 is in contact with a projection 51 (this state will be referred to as "the unused state") is maintained.

With such a spring member 91 provided, it is possible to prevent unintentional relative movements of the holding part 41 and the outer tube 2, for example, a distal or proximal movement of the outer tube 2 relative to the holding part 41 due to its own weight when the holding part 41 is held. Consequently, operability and safety of the syringe 1A are enhanced.

Incidentally, when an external force of more than a predetermined value in a direction for causing the pressure part 42 and the gasket 3 to approach each other is exerted on at least one of the outer tube 2 and the holding part 41, the spring member 91 is contracted, whereby the pressure part 42 is enabled to press the gasket 3. The spaced state of the pressure part 42 and the gasket 3 from each other can be maintained until the external force of more than the predetermined value is exerted in this manner, operability and safety of the syringe 1A are enhanced, as will be described later.

In addition, in the unused state, the spring member 91 may be in a natural state or in a contracted state (exclusive of a fully contracted state). Preferably, however, the spring member 91 is in a contracted state in the unused state. This ensures that the flange 27 and the projection 51 are pressed against each other, whereby the spaced state of the pressure part 42 and the gasket 3 can be maintained more assuredly.

The configuration of the syringe 1A in this embodiment has thus been described in detail above.

Now, an example of a method of using the syringe 1A will be described below, based on FIG. 6.

First, an intracutaneous needle 200 is attached to the reduced-diameter part 22 of the outer tube 2. As a result, a syringe assembly (syringe assembly according to the present invention) 400A is obtained.

Next, as shown in FIG. 6(*a*), while holding the holding part 41, the needle body 220 is made to puncture a skin in a direction substantially orthogonal to the skin surface.

In this instance, due to resistance generated by puncturing of the skin with the needle body 220, an external force G1 in the direction for contraction of the spring member 91 is exerted on the spring member 91 through the outer tube 2. However, under the external force G1, the spring member 91 would not be contacted, or, if it is contracted, the length of contraction (the difference between the length of the spring member 91 before contraction and its length after contraction) would be shorter than the spacing distance L1 between the pressure part 42 and the gasket 3 in the unused state. Specifically, when the needle body 220 is only made to puncture the skin, the gasket 3 is not pressed by the pressure part 42 but is maintained at the position in the unused state. This ensures that the liquid medicine 100 is prevented from being ejected via the needle body 220 before the needle body 220 punctures the skin completely.

In other words, the hardness (elastic force) of the spring member 91 is so set that the spring member 91 would not be contracted under the external force G1, or, even if it is contracted, the length of contraction would be shorter than a spacing distance L1 between the pressure part 42 and the gasket in the unused state. This ensures that the above-mentioned effect is exhibited, whereby operability and safety of the syringe 1A are enhanced.

Next, as shown in FIG. 6(*b*), the holding part 41 is pushed toward the skin side. As a result, an external force G2 in the same direction as the external force G1 and greater than the external force G1 is exerted on the outer tube 2, whereby the spring member 91 is contracted and the holding part 41 is moved distally relative to the outer tube 2. Attendant on the movement of the holding part 41, the pressure part 42 approaches the gasket 3, and the pressure part 42 comes into contact with the gasket 3. Thus, when the external force G2 is exerted, the spaced state of the pressure part 42 and the gasket 3 is released.

Subsequently, as shown in FIG. 6(c), the holding part 41 is pushed further toward the skin side, whereon the gasket 3 is moved distally by the pressure applied by the pressure part 42. As a result, the liquid medicine 100 stored in the outer tube 2 is injected into the skin through the distal end of the needle body 220.

Finally, for withdrawing the needle body 220 from the skin, the holding part 41 is moved away from the skin surface. As above-mentioned, the used state is maintained by the spring member 91 and the projection 61. Therefore, when the needle body 220 is withdrawn from the skin, the outer tube 2 and the holding part 41 are prevented from being displaced in an unintentional manner, so that the needle body 220 can be withdrawn safely. Accordingly, operability and safety of the syringe 1A are enhanced.

The syringe 1A as above-mentioned ensures that puncture of the skin by the needle body 220 and administration of the liquid medicine 100 can be performed by only the operation of holding the holding part 41 and pressing it toward the skin side. In addition, since the relative positional relationship between the holding part 41 and the outer tube 2 can be maintained by the spring member 91, puncturing of the skin by the needle body 220 and the like operations can be carried out safely.

<Third Embodiment>

Now, a third embodiment of the present invention will be described below.

Figure 7:
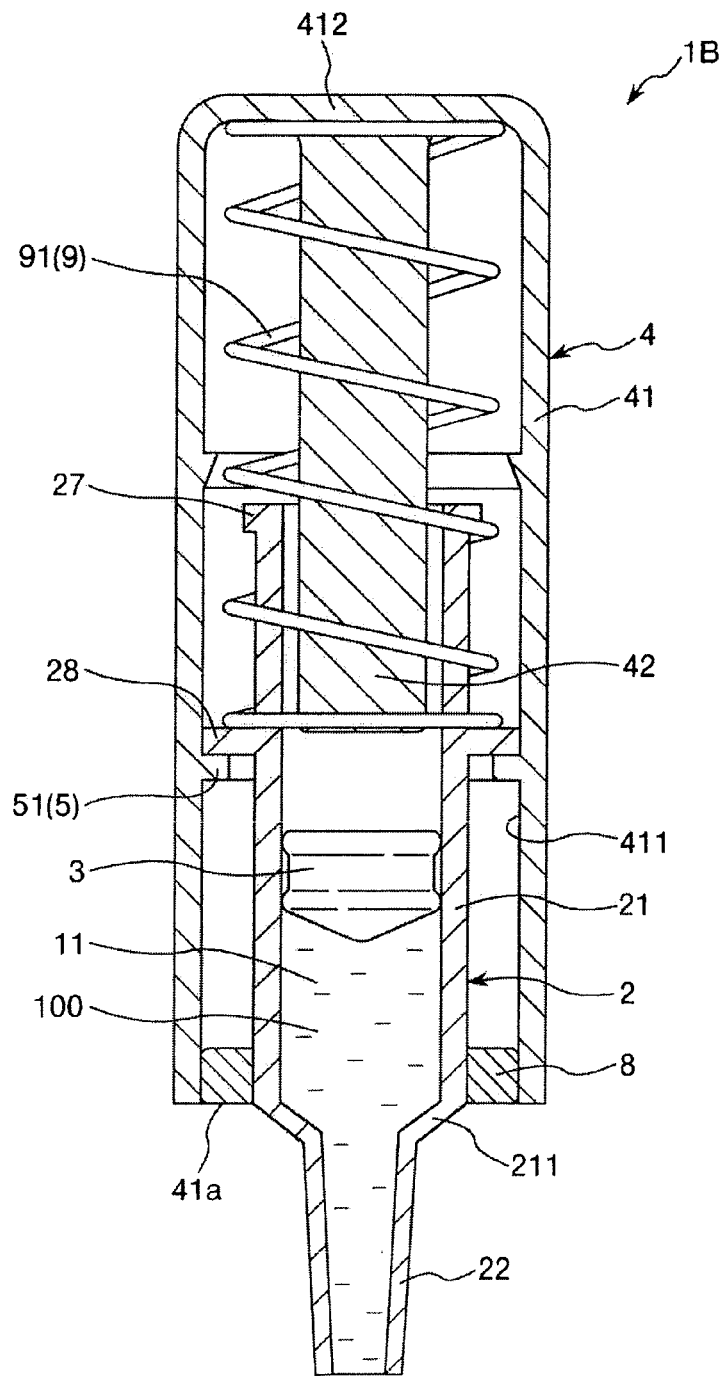
FIG. 7 is a longitudinal sectional view showing a third embodiment of a syringe according to the present invention.
Figure 8:
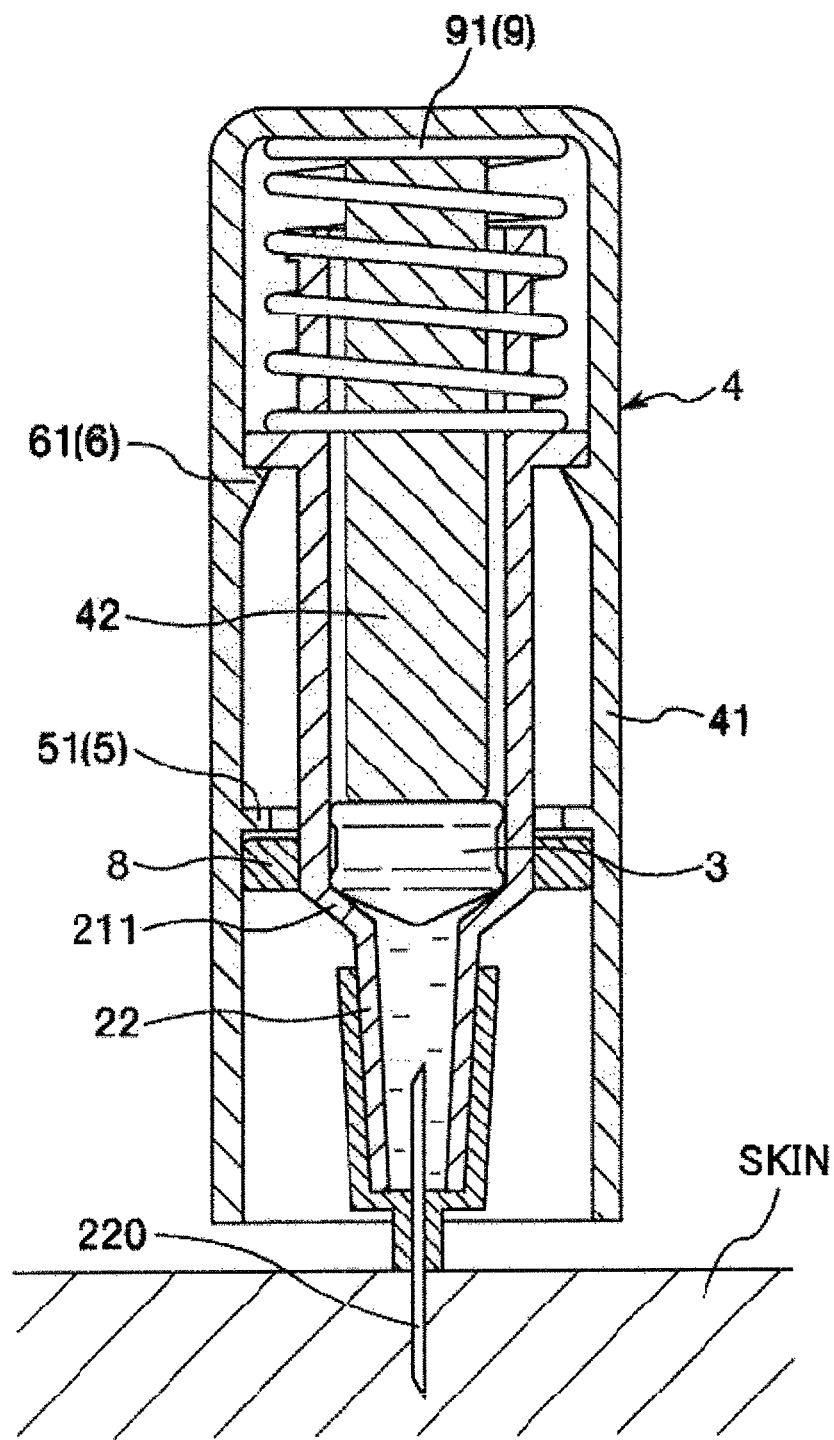
FIG. 8 is a longitudinal sectional view showing a state in use of a syringe assembly in which the syringe shown in FIG. 7 is used.

FIG. 7 is a longitudinal sectional view showing a third embodiment of a syringe according to the present invention, and FIG. 8 is a longitudinal sectional view showing a used state of a syringe assembly in which the syringe shown in FIG. 7 is employed.

Now, the syringe according to this embodiment will be described below. The following description will be made to center on differences from the syringe according to the second embodiment above, and descriptions of the same items as those in the second embodiment will be omitted.

The syringe according to this embodiment is substantially the same as the syringe according to the second embodiment above, except for the difference in positions where detachment-preventing means and state-maintaining means are formed.

As shown in FIG. 7, in the syringe 1B in this embodiment, an outer tube is formed, on a distal side relative to a flange 27, with a flange 28 projecting at an outer surface thereof. In addition, a holding part 41 is formed, on the distal side relative to the flange 28, with a projection 51 which constitutes detachment-preventing means 5. The contact of the flange 28 with the projection 51 ensures that the outer tube 2 cannot move further toward a side of an opening 41a. As a result, detachment of the outer tube 2 from the holding part 41 is prevented.

Incidentally, in this embodiment, the projection 51 is provided at a position which is deviated toward the opening 41a side of the holding part 41, as compared with that in the above-described second embodiment.

In addition, a projection 61 constituting state-maintaining means 6 is provided to be located, in the unused state, on a proximal side relative to that portion of an inner wall 411 which makes contact with the flange 28. Then, as shown in FIG. 8, after the flange 28 gets over the projection 61 as the holding part 41 is moved distally relative to the outer tube 2, the contact of the flange 28 with the projection 61 restrains the holding part 41 from moving proximally relative to the outer tube 2. As a result, the used state is maintained.

Besides, a spring member 91 constituting biasing means 9 is provided inside the holding part 41, and between a bottom part 412 of the holding part 41 and the flange 28 of the outer tube 2. The spring member 91 biases the outer tube 2 distally relative to the holding part 41, whereby a state in which the flange 28 is in contact with the projection 51 (the unused state) is maintained. Incidentally, the spring member 91 has an outside diameter smaller than an inside diameter of the projection 61, so as to avoid contact thereof with the projection 61. In addition, the flange 27 has an outside diameter smaller than an inside diameter of the spring member 91, so as not to hamper the disposition of the spring member 91. As a result, mutual catching between the spring member 91 and the flange 27 and mutual catching of the spring member 91 and the projection 61 can both be prevented, so that the syringe 1B can be operated smoothly.

Here, with the projection 51 formed at a position on the holding part 41 closer to the opening 41a, as in this embodiment, a spacing distance of a bottom part 412 and the flange 28 in the unused state can be set long. Therefore, a spring member 91 which is longer, greater in diametrical size and stronger in biasing force can be disposed between the bottom part 412 and the flange 28. For example, the biasing force of the spring member 91 can be enlarged, as compared with that in the second embodiment. In addition, in the case where the spring member 91 is disposed between the bottom part 412 and the flange 28 in a contracted state, the rate of contraction thereof can be set lower than in the second embodiment. Accordingly, disposition of the spring member 91 is facilitated.

Especially, the projection 51 is preferably so formed as to make contact with a guide part 8 or be located near the guide part 8, in the used state shown in FIG. 8. This ensures that the spacing distance between the bottom part 412 and the flange 28 in the unused state can be made longer. As a result, the above-mentioned effect can be exhibited more effectively.

Besides, the spacing distance between the bottom part 412 and the flange 28 in the unused state can be made longer also by forming the guide part 8 at a position closer to the opening 41a, as shown in FIG. 8. As shown in FIG. 8, the guide part 8 in this embodiment is so provided that its lower face coincides with the opening 41a.

<Fourth Embodiment>

Now, a fourth embodiment of the syringe according to the present invention will be described below.

Figure 9:
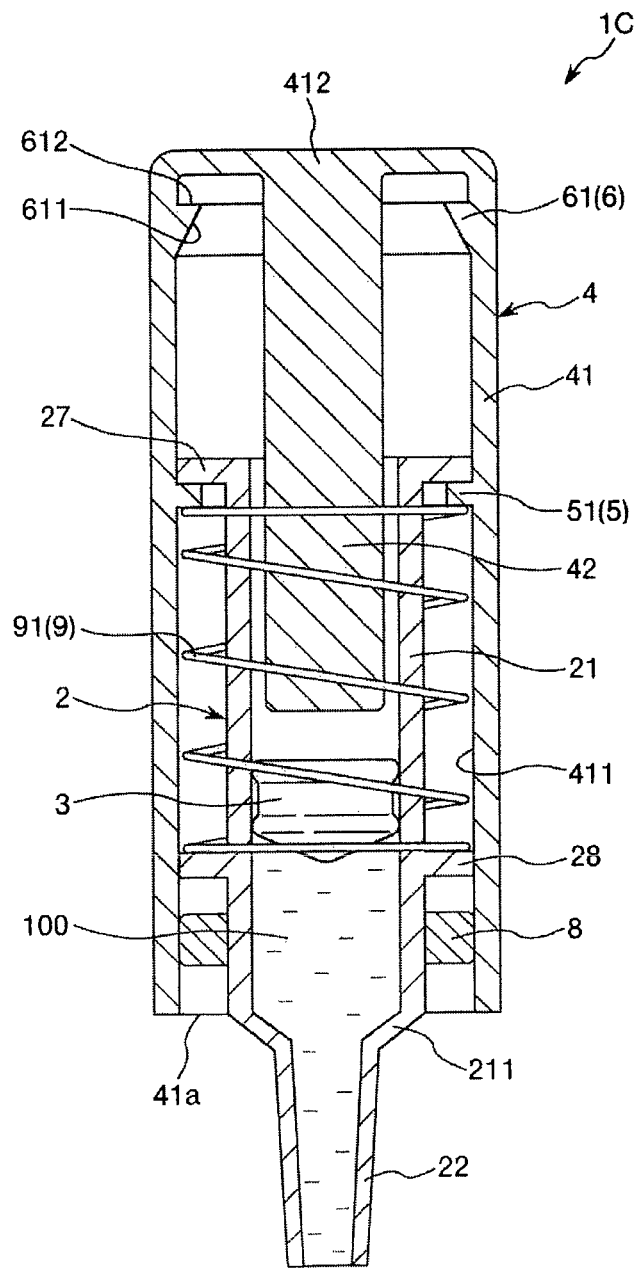
FIG. 9 is a longitudinal sectional view showing a fourth embodiment of a syringe according to the present invention.
Figure 10:
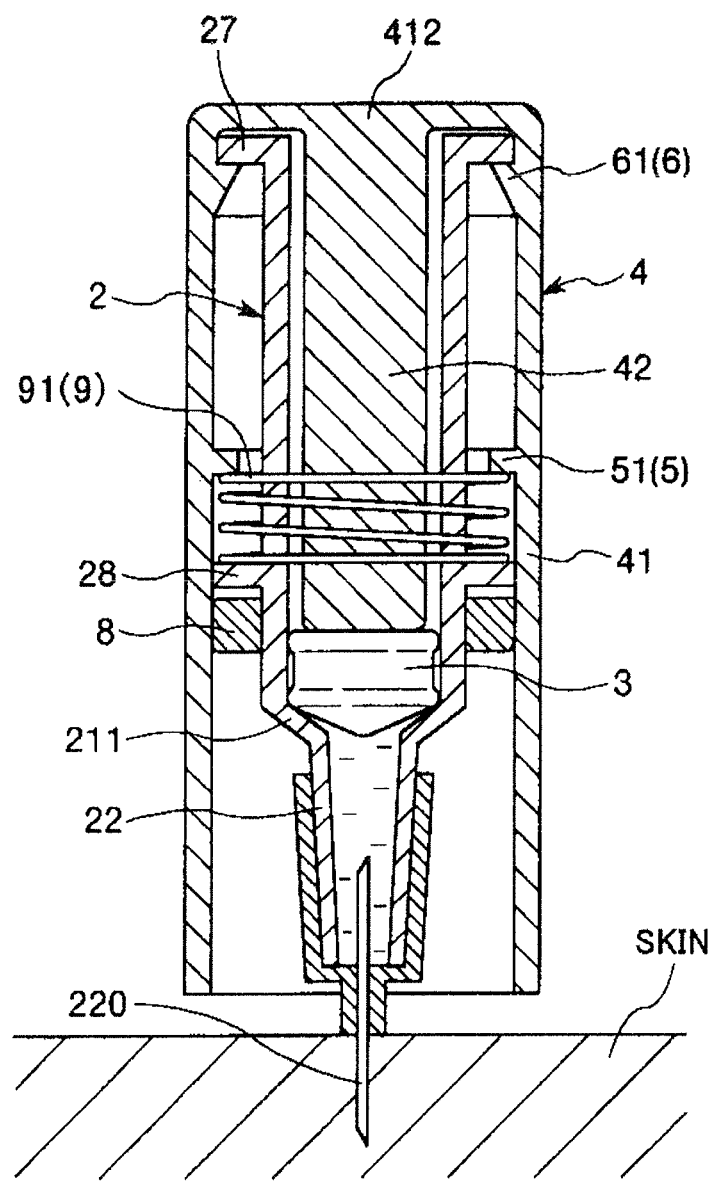
FIG. 10 is a longitudinal sectional view showing a state in use of a syringe assembly in which the syringe shown in FIG. 9 is used.

FIG. 9 is a longitudinal sectional view showing a fourth embodiment of a syringe according to the present invention, and FIG. 10 is a longitudinal sectional view showing a used state of a syringe assembly in which the syringe shown in FIG. 9 is employed.

Now, the syringe according to this embodiment will be described below. In the following, the description will be made to center on differences from the syringe according to the second embodiment above, and descriptions of the same items as those in the second embodiment will be omitted.

The syringe according to this embodiment is substantially the same as the syringe according to the second embodiment, except for difference in the layout of biasing means (spring member).

As shown in FIGS. 9 and 10, in the syringe 10 according to this embodiment, an outer tube 2 is formed, on a distal side relative to a flange 27, with a flange 28 projecting from an outer surface thereof. In addition, a spring member 91 constituting biasing means 9 is provided between the flange 28 and a projection 51 formed on a holding part 41. The spring member 91 biases the outer tube 2 distally relative to the holding part 41, whereby a state in which the flange 27 is in contact with the projection 51 (the unused state) is maintained.

According to such a configuration, the overall length of the syringe 10 can be shortened, as compared with that in the second embodiment, for example. Specifically, in the above-described second embodiment, a space for accommodating the spring member 91 and the flange 27 has to be secured between the bottom part 412 of the holding part 41 and the projection 61. In this embodiment, on the other hand, it suffices that a space for accommodating the flange 27 is only secured between the bottom part 412 and the projection 61. In other words, it is unnecessary to secure an accommodation space for the spring member 91 and, therefore, the overall length of the syringe 1C can be shortened accordingly, as compared with the second embodiment.

While the syringe according to the present invention has been described above with reference to some embodiments shown in the drawings, the invention is not to be restricted to the embodiments. The components of the syringe can be replaced by those of arbitrary configurations which can exhibit the same functions as above-mentioned. Besides, arbitrary structures may be added.

In addition, the syringe according to the present invention may be a combination of arbitrary two or more configurations (features) of each of the above embodiments.

Besides, while the pressure part applies pressure directly to the gasket in the above-described embodiments, this is not restrictive; for example, an intermediate member may be interposed between the gasket and the pressure part. Examples of the intermediate member include a hard (e.g., formed of a resin material or the like) member connected to the gasket. According to such a configuration, the pressure part presses the hard intermediate member and the gasket is moved thereby. Consequently, an excessive deformation of the gasket or the like can be restrained, as compared with the case where the gasket is pressed directly by the pressure part.

In addition, while a configuration in which the pusher and the gasket are spaced from each other in the unused state has been described in the embodiments above, this configuration is not restrictive. For instance, the pusher and the gasket may be in contact with each other in the unused state. In this case, it is preferable in the second to fourth embodiments to adopt a configuration in which the spring member is not contracted even by the external force G1.

Figure 11:
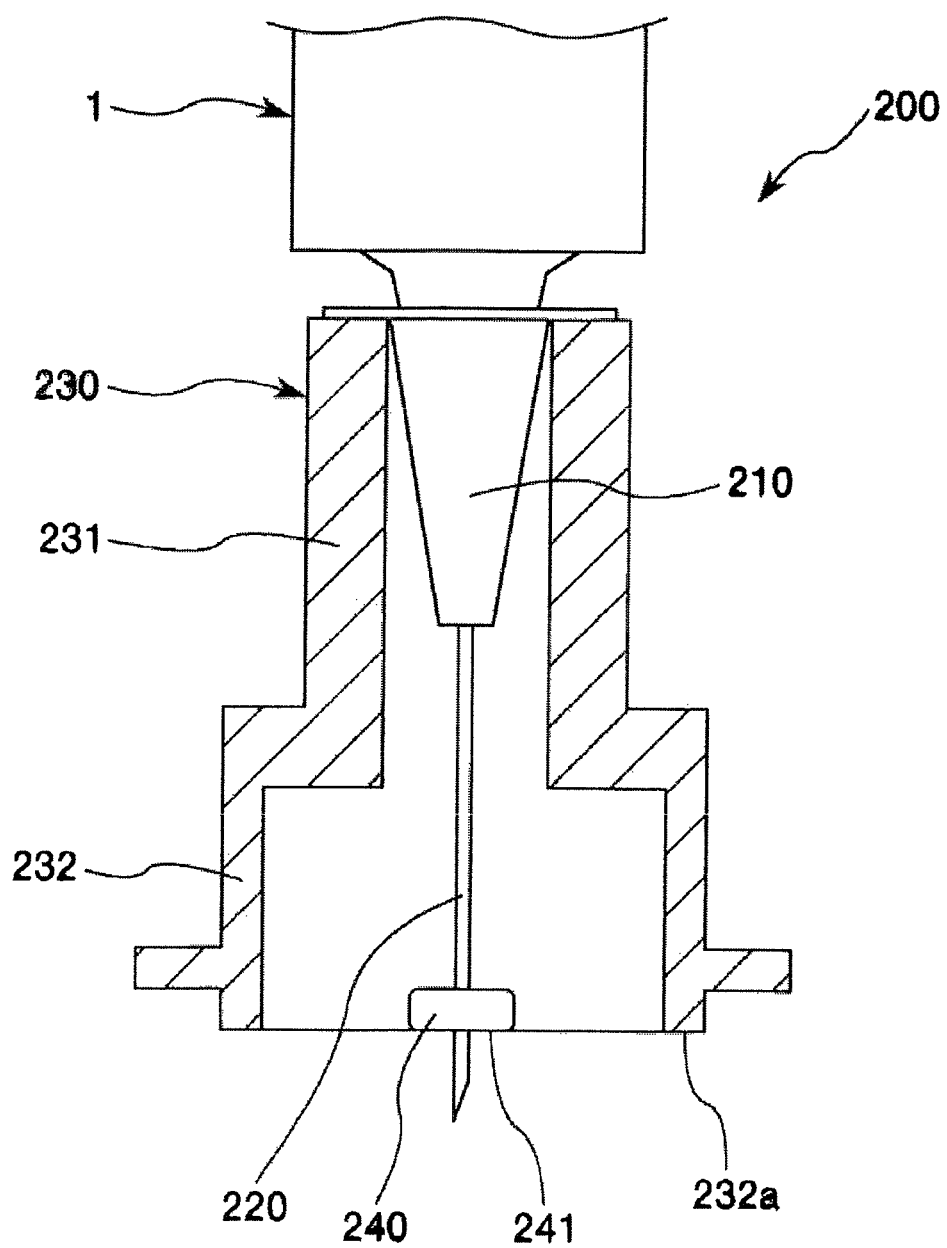
FIG. 11 is a longitudinal sectional view showing a modification of an intracutaneous needle shown in FIG. 3.

Besides, while the intracutaneous needle 200 composed of the hub 210 and the needle body 220 has been described in the above embodiments, the configuration of the intracutaneous needle 200 is not restricted to this one. For example, the intracutaneous needle 200 has a hub 210, a needle body 220, a stability part 230, and an adjustment part 240 as shown in FIG. 11.

The needle body 220 is inserted and passed through the adjustment part 240. The adjustment part 240 is fixed to the needle body 220 by use of an adhesive or the like, for example.

The stability part 230 includes a tubular fixing part 231, and a tubular contact part 232 provided on a distal side of the fixing part 231. The fixing part 231 is so provided as to cover the hub 210, and the stability part 230 is fixed to the hub 210 through the fixing part 231. The contact part 232 is so provided as to cover the periphery of the needle body 220 and the adjustment part 240. Besides, an inside diameter of the contact part 232 is set to be greater than an inside diameter of the fixing part 231.

In addition, a distal-side end face 232a of the contact part 232 is located substantially on the same plane as a needle projection face (lower face) 241 of the adjustment part 240. The needle body 220 is orthogonal to a plane formed by the end face 232a and the needle projection face 241. Therefore, when the needle body 220 punctures a living body (skin), the needle projection face 241 of the adjustment part 240 makes contact with the surface of the skin, and the end face 232a of the contact part 232 also makes contact with the skin surface. This ensures that the needle body 220 can be supported substantially orthogonally to the skin by the stability part 230. As a result, the needle body 220 can be prevented from being positionally disturbed, and the needle body 220 is enabled to puncture the skin orthogonally.

Incidentally, the needle projection face 241 of the adjustment part 240 may not necessarily be located on the same plane as the end face 232a of the contact part 232. Specifically, the needle projection face 241 of the adjustment part 240 may be located on the proximal side relative to the end face 232a.

INDUSTRIAL APPLICABILITY

According to the present invention, it is possible to provide a syringe and a syringe assembly which are excellent in operability. Specifically, when a puncture needle is made to puncture a skin while holding a holding part, with the puncture needle connected to a port, for example, an outer tube is fixed relative to the skin due to the puncturing of the skin by the puncture needle. With the holding part pushed further toward a skin side, a gasket is moved by a pressure part, whereby a liquid medicine can be administered into the patient's body via the puncture needle. In other words, administration of the liquid medicine is completed in a single step of moving the holding part toward the skin side. In addition, according to such an operating method, the liquid medicine can be injected intracutaneously by use of an arm's force, so that the syringe can be operated with a sufficient force. As a result, a syringe and a syringe assembly excellent in operability are realized. Furthermore, due to the enhanced operability, mistakes in administration and the like can be prevented from occurring, and reliability and safety are also be enhanced. Accordingly, the syringe and the syringe assembly of the present invention are applicable on an industrial basis.

The invention claimed is:

1. A syringe comprising:
an outer tube having a port through which a liquid can flow in and out, and the port provided on a distal side of the outer tube, the port comprising an elongated conduit having a peripheral wall, and a flange provided on an outer surface of a proximal side of the outer tube;
a gasket capable of sliding in the outer tube;
a pusher operated to move the gasket toward the distal side of the outer tube, and
a needle assembly including a hub attached to the port of the outer tube and a needle body supported by the hub, the hub comprising a hollow space defined by an inner surface of the hub;

the conduit is inserted into the hollow space of the hub such that an outer surface of the peripheral wall of the elongated conduit contacts the inner surface of the hub;

wherein the pusher has a tubular holding part configured to cover at least a part of an outer surface of the outer tube and be movable relative to the outer tube in a longitudinal direction of the outer tube, and a pressure part connected with the tubular holding part, inserted into the outer tube, and configured to move the gasket to the distal side of the outer tube by a distal movement of the tubular holding part relative to the outer tube, a detachment preventing projection provided on an inner wall of the tubular holding part on the distal side of the flange for preventing the outer tube from being detached from the tubular holding part, a spaced state maintaining projection provided on the inner wall of the tubular holding part on the proximal side of the detachment preventing projection for maintaining a spaced state of the pressure part and the gasket, a state maintaining projection provided on the inner wall of the tubular holding part on the proximal side of the spaced state maintaining projection for maintaining a state in which the tubular holding part has been moved distally relative to the outer tube, and wherein the port of the outer tube is configured to protrude from a distal end of the tubular holding part so as to enable the hub of the needle to attach to the port of the outer tube.

2. The syringe according to claim 1 comprising a guide part configured to guide the movement of the tubular holding part relative to the outer tube in the longitudinal direction of the outer tube and provided between the tubular holding part and the outer tube.

3. The syringe according to claim 2, wherein the guide part is fixed to one of the outer tube and the tubular holding part, and is in slidable contact with the other.

4. The syringe according to claim 1, wherein the pressure part is spaced from the gasket in the longitudinal direction of the outer tube.

5. The syringe according to claim 4, wherein when an external force of more than a predetermined value for moving the outer tube proximally relative to the tubular holding part is exerted on at least one of the outer tube and the tubular holding part, the spaced state of the pressure part and the gasket is released, and the gasket is moved toward the distal side of the outer tube by the pressure part.

6. The syringe according to claim 5, wherein the predetermined value is set to be greater than an external force exerted on the outer tube when the needle connected to the port is made to puncture a skin, with the tubular holding part being held.

7. The syringe according to claim 1, wherein the port of the outer tube is protruding from a distal-side opening of the tubular holding part.

8. The syringe according to claim 1, comprising:
a housing for storing the needle therein,
wherein the housing has a flange making contact with a distal end face of the tubular holding part when the puncture needle is attached to the port of the outer tube in a state of storing the needle in the housing.

9. A syringe comprising:
an outer tube having a port provided on a distal side of the outer tube, through which a liquid can flow in and out, and a flange provided on an outer surface of a proximal side of the outer tube, the port comprising an elongated conduit having a peripheral wall;
a gasket capable of sliding in the outer tube;
a pusher operated to move the gasket toward the distal side of the outer tube,
a needle assembly including a hub attached to the port of the outer tube and a needle body supported by the hub, the hub comprising a hollow space defined by an inner surface of the hub;
the conduit is inserted into the hollow space of the hub such that an outer surface of the peripheral wall of the elongated conduit contacts the inner surface of the hub; and
wherein the pusher has a tubular holding part configured to cover at least a part of an outer surface of the outer tube and be movable relative to the outer tube in a longitudinal direction of the outer tube, the tubular holding part having a spaced state maintaining projection provided on an inner wall of the tubular holding part, and a pressure part connected with the tubular holding part, inserted into the outer tube, and configured to move the gasket to the distal side of the outer tube by a distal movement of the tubular holding part relative to the outer tube,
wherein by making the spaced stated maintaining projection of the tubular holding part contact the flange of the outer tube, a spaced state of the pressure part and the gasket is maintained,
a detachment preventing projection provided on an inner wall of the tubular holding part on the distal side of the flange for preventing the outer tube from being detached from the tubular holding part, and
a state maintaining projection provided on the inner wall of the tubular holding part on the proximal side of the spaced state maintaining projection for maintaining a state in which the tubular holding part has been moved distally relative to the outer tube.

10. The syringe according to claim 1, wherein an inner surface of the peripheral wall of the elongated conduit is spaced apart from the needle body in a radial direction.

11. The syringe according to claim 9, wherein an inner surface of the peripheral wall of the elongated conduit is spaced apart from the needle body in a radial direction.

* * * * *